US00PP29068P3

(12) United States Plant Patent
Nederpel

(10) Patent No.: US PP29,068 P3
(45) Date of Patent: Mar. 6, 2018

(54) ***CRASSULA* PLANT NAMED 'INDIAN SUMMER'**

(50) Latin Name: *Crassula ovata*
Varietal Denomination: Indian Summer

(71) Applicant: Maurice G. J. Nederpel, Honselersdijk (NL)

(72) Inventor: Maurice G. J. Nederpel, Honselersdijk (NL)

( * ) Notice: Subject to any disclaimer, the term of this patent is extended or adjusted under 35 U.S.C. 154(b) by 0 days.

(21) Appl. No.: 14/999,501

(22) Filed: May 16, 2016

(65) Prior Publication Data

US 2017/0332537 P1 Nov. 16, 2017

(51) Int. Cl.
*A01H 5/00* (2006.01)
*A01H 5/12* (2006.01)

(52) U.S. Cl.
USPC ..... Plt./373
CPC ..... *A01H 5/12* (2013.01)

(58) Field of Classification Search
USPC ..... Plt./373, 372
CPC ..... A01H 5/00; A01H 5/12
See application file for complete search history.

(56) References Cited

PUBLICATIONS

GTITM UPOVROM Citation for 'Indian Summer' as per QZ PBR 20152496; Feb. 15, 2016; 1 page.*

* cited by examiner

*Primary Examiner* — Kent L Bell

(57) ABSTRACT

A new cultivar of *Crassula* plant named 'Indian Summer' that is characterized by obovate shaped leaves that are yellow-green on the upper side when young and that turn grey-red toward the margins during autumn on outdoor grown plants.

1 Drawing Sheet

Botanical classification: *Crassula ovata.*
Variety denomination: 'Indian Summer'.

BACKGROUND OF THE INVENTION

The present invention relates to a new and distinct cultivar of *Crassula* plant botanically known as *Crassula ovata* and hereinafter referred to by the cultivar name 'Indian Summer'.

'Indian Summer' was discovered as a naturally occurring branch mutation of *Crassula ovata* 'Sunset' (not patented). 'Indian Summer' was discovered in 2008 on a plant of *Crassula* 'Sunset' grown in a greenhouse in a cultivated area of Honselersdijk, Netherlands.

Asexual reproduction of the new cultivar 'Indian Summer' first occurred by leaf cuttings in 2010 in Honselersdijk, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Crassula* cultivar 'Indian Summer'. These traits in combination distinguish 'Indian Summer' as a new and distinct cultivar apart from other existing varieties of *Crassula* known by the inventor.

1. *Crassula* 'Indian Summer' exhibits obovate shaped leaves.
2. *Crassula* 'Indian Summer' exhibits young leaves that are yellow-green on the upper side.

3. *Crassula* 'Indian Summer' exhibits leaves that turn grey-red toward the margins during autumn on outdoor grown plants. The leaves of indoor grown plants do not turn grey-red toward the margins.

The closest comparison cultivars are the parent plant *Crassula* 'Sunset' and *Crassula* 'Minor' (not patented). 'Indian Summer' is distinguishable from the parent plant *Crassula* 'Sunset' by the following characteristics:

1. *Crassula* 'Indian Summer' exhibits leaves that are smaller than the leaves of *Crassula* 'Sunset'.
2. *Crassula* 'Indian Summer' exhibits young leaves that are yellow-green on the upper side. The young leaves of *Crassula* 'Sunset' are green on the upper side.
3. *Crassula* 'Indian Summer' exhibits leaves that turn grey-red toward the margins during autumn on outdoor grown plants. The leaves of *Crassula* 'Sunset' have margins that are lighter grey-red during autumn.

'Indian Summer' is distinguishable from *Crassula* 'Minor' by the following characteristics:

1. *Crassula* 'Indian Summer' exhibits leaves that are larger than the leaves of *Crassula* 'Minor'.
2. *Crassula* 'Indian Summer' exhibits young leaves that are yellow-green on the upper side. The young leaves of *Crassula* 'Minor' are bronze in color on the upper side.

BRIEF DESCRIPTION OF THE DRAWING

The accompanying photograph illustrates the distinguishing traits of *Crassula* 'Indian Summer'. The photograph shows an overall view of a 14 month old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Crassula* cultivar named 'Indian Summer'. Data was collected in Honselersdijk, Netherlands from 14 month old plants grown in a glass greenhouse in 10.5 cm. diameter containers. The time of year was October and the temperature range was 20-25 degrees Centigrade during the day and 10-15 degrees Centigrade at night. The light level was natural light level. No photoperiodic treatments or growth retardants were used. Color determinations are in accordance with The Royal Horticultural Society Colour Chart 2007 edition, except where general color terms of ordinary dictionary significance are used. The growing requirements are similar to the species. 'Indian Summer' has not been tested under all possible conditions and phenotypic differences may be observed with variations in environmental, climatic, and cultural conditions, however, without any variance in genotype.

Botanical classification: *Crassula ovata* 'Indian Summer'.
Annual or perennial: Perennial.
Parentage: 'Indian Summer' is a naturally occurring branch mutation of *Crassula* Sunset'.
Plant type: Pot plant.
Plant shape: Flattened spherical.
Growth habit: Broad upright.
Suitable container size: 10.5 cm. pots or larger.
Plant height: 11.2 cm.
Plant width: 16.0 cm.
Vigor: Low.
Low temperature tolerance: 0° Centigrade.
High temperature tolerance: 40° Centigrade.
Propagation: Leaf cuttings.
Time to initiate roots (summer): 30 days at 15-20° C.
Time to initiate roots (winter): 45 days at 10-15° C.
Time to produce a rooted cutting (summer): 60 days at 15-20° C.
Time to produce a rooted cutting (winter): 80 days at 10-15° C.
Crop time: Approximately 60 weeks from rooted cutting in Kudelstaart, Netherlands.
Root system: Fine, fibrous.
Root color: N155.
Plant fragrance: None.
Stem:
- *Branching.*—Basal and lateral branching.
- *Number of primary branches.*—Average 2.
- *Number of lateral branches per primary branch.*—Average 4.
- *Lateral branch dimensions.*—6.6 cm. in length and 1.0 cm. in diameter.
- *Internode length.*—1.4 cm.
- *Stem shape.*—Rounded.
- *Stem texture.*—Glabrous, succulent.
- *Stem pubescence.*—Absent.
- *Stem aspect.*—30 degrees from vertical.
- *Stem strength.*—Strong.
- *Stem color* (*young*).—147D.
- *Stem color* (*mature*).—143B to 143C with narrow ridge at internodes 161D.
- *Pinching.*—No.

Foliage:
- *Leaf arrangement.*—Opposite.
- *Compound or single.*—Single.
- *Leaf dimensions.*—4.2 cm. in length and 2.4 cm. in width.
- *Leaf thickness.*—1.1 cm.
- *Leaf shape.*—Obovate.
- *Leaf apex.*—Broad acute.
- *Leaf base.*—Acuminate.
- *Leaf margin.*—Entire.
- *Texture.*—Glabrous both surfaces, succulent.
- *Leaf luster.*—Glossy both surfaces.
- *Pubescence.*—Absent.
- *Venation pattern.*—None visible.
- *Young leaf color* (*upper surface*).—Between 150C and 151D, margins toward tip 185B.
- *Young leaf color* (*lower surface*).—Between 145B and 150B, margins toward tip 185B.
- *Mature leaf color* (*upper surface*).—NN137B, margins toward tip 183C.
- *Mature leaf color* (*lower surface*).—147B, margins toward tip 187A to 187B.
- *Autumn leaf color on outdoor grown plants* (*upper surface*).—137B to 137C, tinged 180C, more intense toward margins and tip.
- *Autumn leaf color on outdoor grown plants* (*lower surface*).—143C, upper 30% of leaf tinged 185A, more intense toward margins and tip.
- *Durability of foliage to stress.*—High.
- *Leaf attachment.*—Sessile.

Flower: 'Indian Summer' has not produced flowers to date.
Fruit and seed: Fruit or seed production has been observed to date.
Disease and pest resistance: Disease and pest resistance has not been observed to date.

The invention claimed is:

1. A new and distinct variety of *Crassula* plant named 'Indian Summer' as described and illustrated.

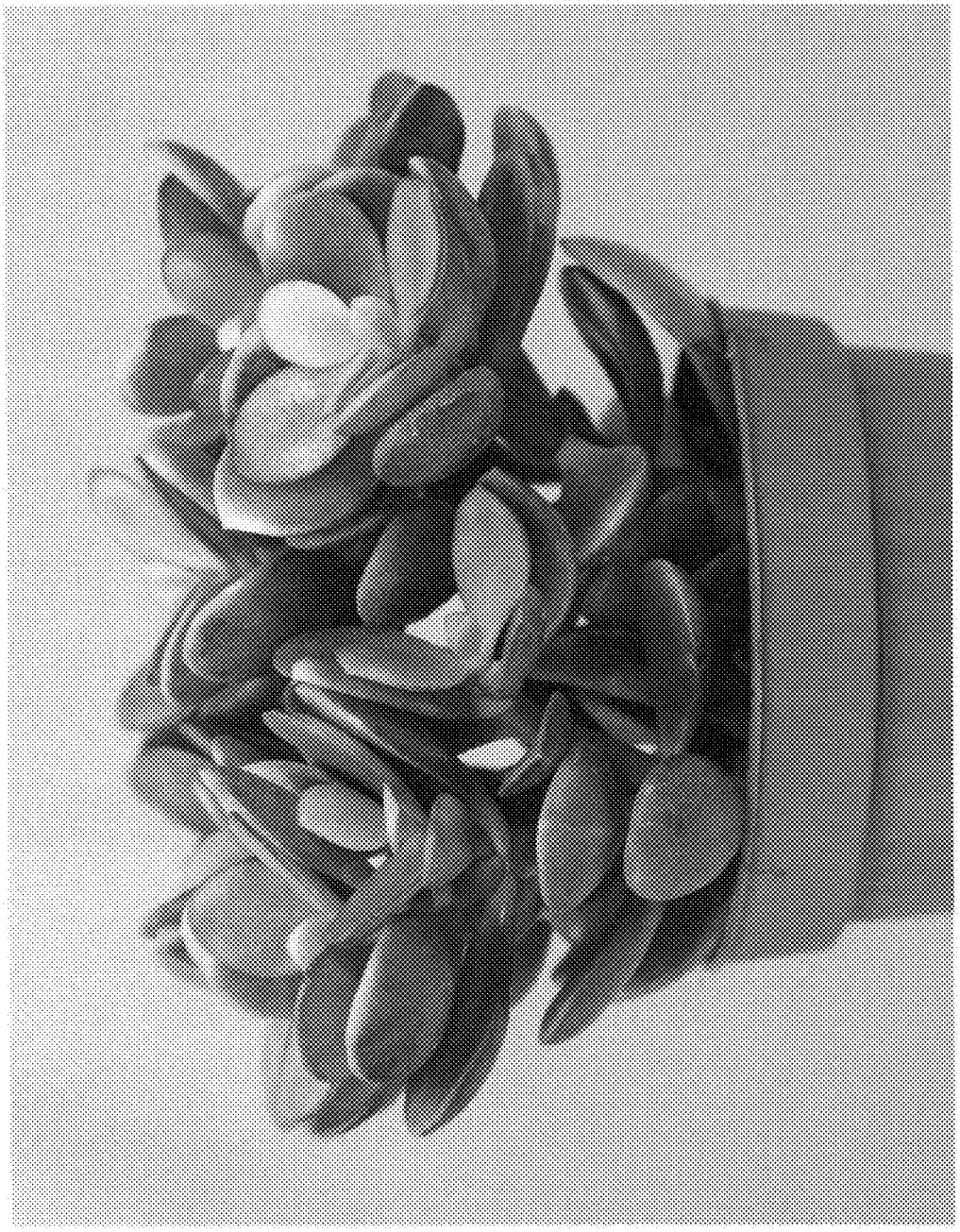

* * * * *